July 8, 1952 E. S. BOERNER Plant Pat. 1,113
CHRYSANTHEMUM PLANT
Filed May 25, 1951
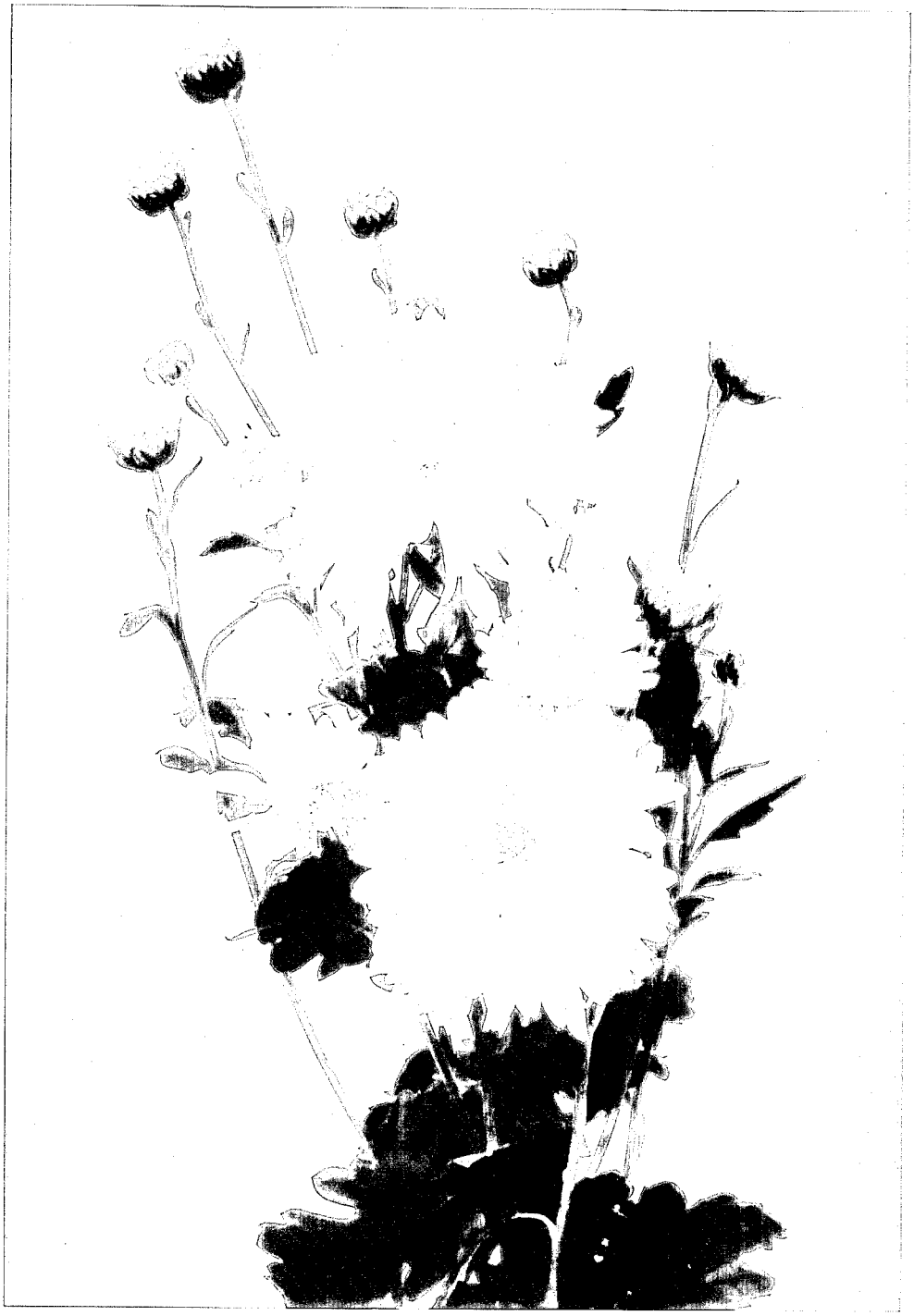
Inventor.
E. S. Boerner
By: Robert Cobb
Attorneys.

Patented July 8, 1952

Plant Pat. 1,113

UNITED STATES PATENT OFFICE 1,113

CHRYSANTHEMUM PLANT

Eugene S. Boerner, Newark, N. Y., assignor to Jackson & Perkins Company, Newark, N. Y., a corporation of New York Application May 25, 1951, Serial No. 228,239

1 Claim. (Cl. 47—60)

The present invention relates to a new and distinct variety of chrysanthemum plant, originated by me by crossing the unpatented variety known as "Avalanche" with an unnamed and unpatented large-flowered pompom type yellow seedling identified in my breeding and planting records as #4508-3.

The primary objective in making this cross was to obtain a larger, earlier and hardier flowering outdoor chrysanthemum than has heretofore been available. Accordingly, the decorative type "Avalanche" was used as one parent, and a large, yellow, pompom type seedling was used as the other parent, and this cross fully achieved the desired objective, as evidenced by the following dominant and unique combination of characteristics which definitely distinguish this new variety from the parents, as well as from all other known varieties:

(1) Improved hardiness superior to that of prior chrysanthemums of the pompom type;

(2) Larger semi-pompom type flowers of Light Cadmium color in general tonality;

(3) Crisp petals;

(4) Long-lasting quality of the flowers;

(5) Freedom and continuity of bloom.

Asexual reproduction of this new variety by top cuttings and also by underground runners at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed at Newark, New York, with color terminology in accordance with Ridgway's Color Standards and Nomenclature:

Parentage: "Avalanche" × an unnamed large-flowered yellow pompom type seedling.

Classification: Semi-pompom; large; flower does not extend fully back as in true pompom.

Growth: Clean, upright growth—attaining a height of 24 inches.

Cold resistance: Winter hardy and the flowers burn very slightly with frost, but they are not destroyed.

Blooming period: In the Newark, New York, climatic area, average date of start of bloom is September 8th—bloom continues until severe freezing in October and November.

Bud:

*Color.*—When sepals first divide—Empire Yellow, Plate 4. When petals begin to unfurl—Light Cadmium, Plate 4. When half blown—inside of petals: Light Cadmium, Plate 4; reverse of petals: Apricot Yellow, Plate 4.

*Peduncle.* — Color — Jade Green, Plate 31. Strength—slender; erect.

Bloom:

*Size.*—3½ to 4 inches.

*Stem.*—Strong; normal.

*Form.*—Semi-pompom.

*Petalage.*—Very double.

*Color.*—Center of flower—Light Cadmium, Plate 4. Outer petals—Buff Yellow, Plate 4. Base of petals—Baryta Yellow, Plate 4. Inside of petals—Apricot Yellow, Plate 4. Reverse of petals—Buff Yellow, Plate 4. General tonality—Light Cadmium, Plate 4.

*Petals.*—Texture—stiff. Form—oval.

Fragrance: Lemon Verbena.

Plant:

*Form.*—Rounded; upright.

*Growth.*—Vigorous.

Foliage:

*Size.*—Medium.

*Quantity.*—Normal.

*Color.*—Upper side—Dark Cress Green, Plate 31; reverse side—Cress Green, Plate 31.

*Texture.*—Leathery.

I claim:

A new and distinct variety of chrysanthemum plant of the semi-pompom class, characterized as to novelty by its improved hardiness, by its larger semi-pompom type flowers of Light Cadmium color in general tonality, by the crisp petals of its flowers and the long-lasting quality of its flowers, and by its freedom and continuity of bloom, substantially as herein shown and described.

EUGENE S. BOERNER.

No references cited.